US00PP30666P3

(12) United States Plant Patent
Shipley

(10) Patent No.: US PP30,666 P3
(45) Date of Patent: Jul. 9, 2019

(54) GREGG ASH TREE NAMED 'LIBBY DAVIDSON'

(50) Latin Name: *Fraxinus greggii*
Varietal Denomination: Libby Davidson

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 15/732,362

(22) Filed: Oct. 31, 2017

(65) Prior Publication Data

US 2019/0133012 P1 May 2, 2019

(51) Int. Cl.

| | |
|---|---|
| ***A01H 5/02*** | (2018.01) |
| ***A01H 6/00*** | (2018.01) |
| ***A01H 5/04*** | (2018.01) |

(52) U.S. Cl.
USPC ..... Plt./219
CPC ..... *A01H 6/00* (2018.05); *A01H 5/04* (2013.01)

(58) Field of Classification Search
USPC ..... Plt./219, 213, 226
CPC ..... A01H 5/12; A01H 5/02
See application file for complete search history.

(56) References Cited

PUBLICATIONS www.arizonensis.org/bigtrees/arizona_champs.html; Arizona Registry of Big Trees; Arizona's National Champion Trees; Jun. 2005; 9 pages.*

* cited by examiner

*Primary Examiner* — Kent L Bell

(57) ABSTRACT

A new and distinct *Fraxinus greggii* tree named 'Libby Davidson' is characterized by unusually large, dark green leaves, improved growth rate, improved cold hardiness and is more evergreen than other available Gregg ash.

6 Drawing Sheets

Latin name: *Fraxinus greggii.*
Varietal denomination: 'Libby Davidson'.

INTRODUCTION

The genus *Fraxinus*, commonly known as ash trees (or shrubs) belongs to the olive family, Oleaceae, consisting of somewhere in the neighborhood of 45-65 species distributed worldwide in the continents of North America, Asia and Europe. Many species of ash are useful for their wood products, as well as for use in landscape plantings. The Section Pauciflorae (E. Wallander) contains about 5 species (Some possible synonymies are still unresolved.) native to arid and semiarid regions of the Southwestern United States, Mexico and parts of Central America. All the Pauciflorae are shrubs or small trees. The leaves are small and coriaceous with winged rachi. The flowers are apetalous and wind pollinated. *Fraxinus greggii*, Gregg Ash, is found primarily along the Rio Grande Valley of Southern New Mexico and Texas. Another disjunct distribution is reported from southern Chihuahua and Coahuila south to San Luis Potosi. Gregg Ash has been widely grown as a large landscape shrub or small tree in the Southwestern United States. The plants eventually grow to about 20 feet tall×20 feet wide in the landscape without pruning. The plants have fairly thin branches and can be hedged. Gregg Ash is generally considered to be low-moderate in water use and fairly slow in growth, generally around 1-1.5 feet per year. The plants are evergreen.

BACKGROUND OF THE INVENTION

Wild Gregg Ash, though attractive in the landscape and drought resistant, presents some problems to the nursery industry, as the growth rate, adaptability, color, growth form and leaves vary widely. This creates a nonuniform appearance in mass plantings, parking lots and so on. Additionally, perhaps 20% of wild seedlings grow poorly and must be discarded.

The present invention relates to a new and distinct cultivar of *Fraxinus greggii*. The cultivar originated as a seedling in a 2006 growout of *Fraxinus greggii* seeds gathered from existing nursery plants. About 500 seedlings were grown in a cultivated area near Sahuarita, Ariz. Of these seedlings, one plant proved to be faster growing, with larger and darker green leaves than the other seedlings. This cultivar is evergreen and has not exhibited any frost damage in 10 years of growth at the Sahuarita location and is the object of this application.

SUMMARY OF THE INVENTION

Among the features that distinguish the new *Fraxinus greggii* cultivar from all other available and commercial varieties of Gregg Ash known to the inventor are the following combination of characteristics: Fast growth for the species; larger, darker green leaves than typical for the species; better frost hardiness (at least 10° F. without defoliation) than typical for the species; improved evergreen tendency for the species; and ultimately a larger mature plant size than is typical for *Fraxinus greggii*.

The propagation procedure is as follows: Young hardwood cuttings are prepared from the terminal one foot of branches near the end of summer. These are further cut into 4" long×2-3 mm thick pieces with the lower nodes deleafed, then placed into a 5:1 solution (water:rooting compound) of DIP'N GRO™ for 15 seconds, followed by planting in trays filled with JIFFY™ PREFORMA™. Trays of cuttings are moved to a fog propagation house located at a commercial nursery near Sahuarita, Ariz., maintained at 85-90% relative humidity and temperatures varying from 65-85° F. Cuttings root in about 8 weeks.

The foregoing characteristics and distinctions come true to form and are established and transmitted through succeeding asexual propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Fraxinus greggii* "Libby Davidson' growing near Sahuarita, Ariz., depicted in color as nearly correct as it is possible to make in a color illustration of the character.

DETAILED PLANT DESRIPTION

Figure 1:
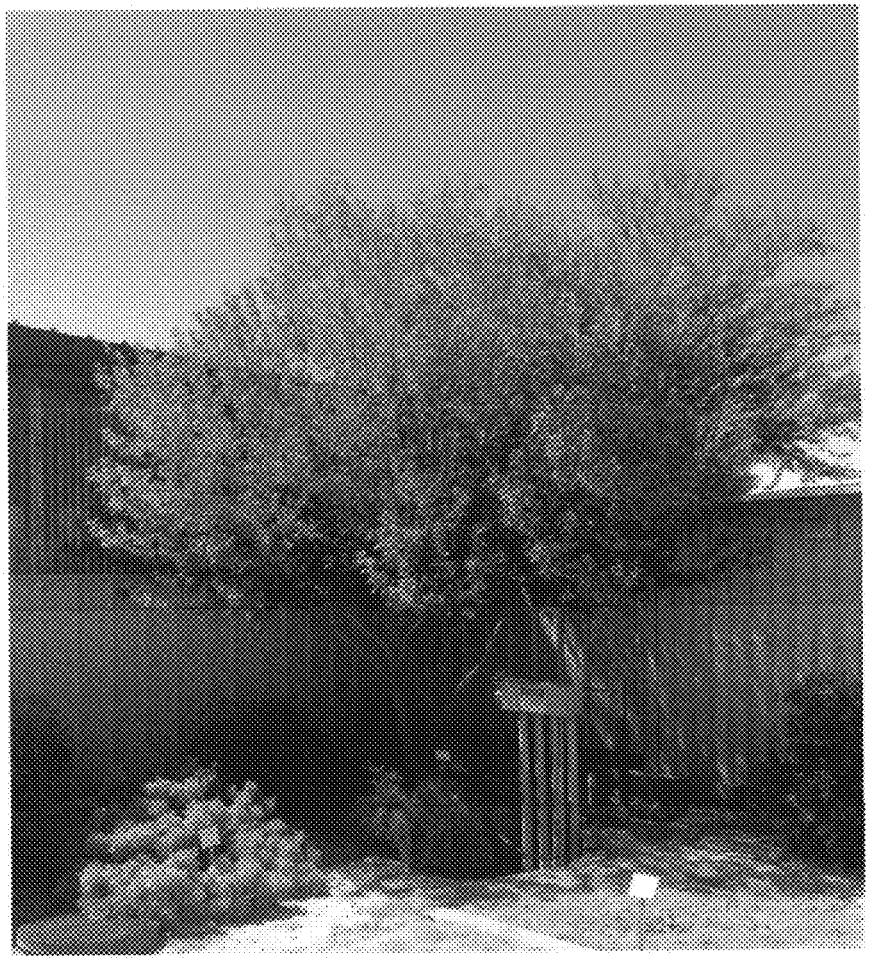
FIG. 1 shows *Fraxinus greggii* 'Libby Davidson' growing near Sahuarita, Ariz. at age 10.
Figure 2:
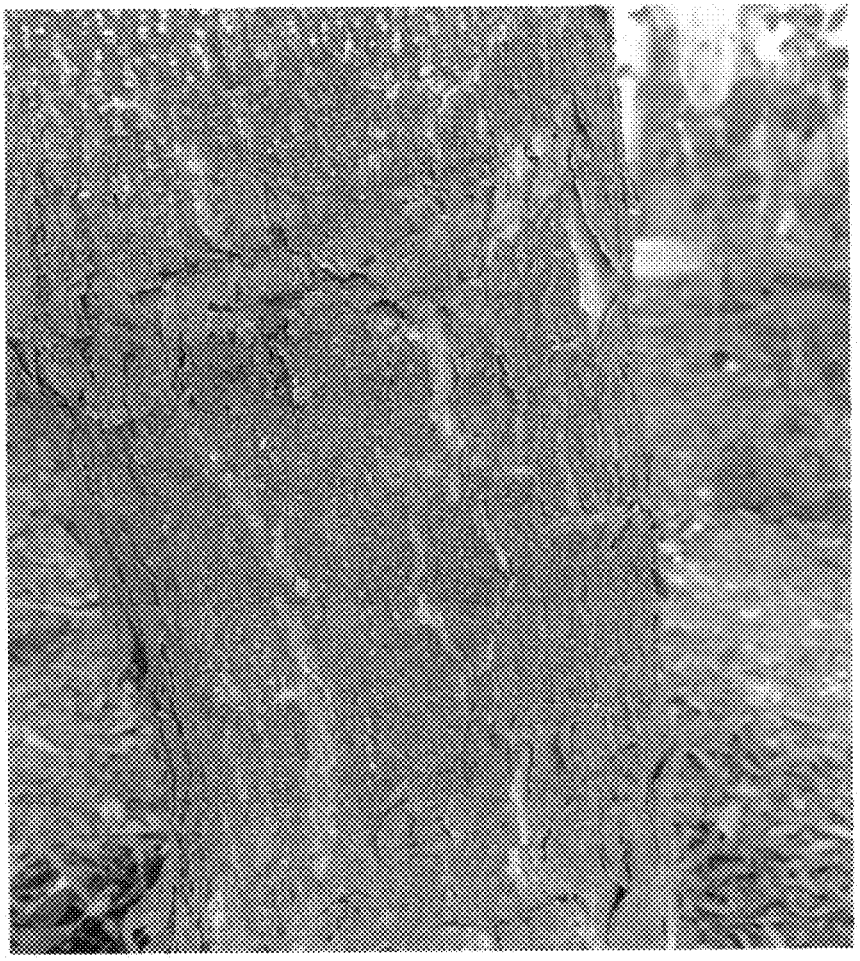
FIG. 2 shows the main trunk of the tree illustrated in FIG. 1.
Figure 3:
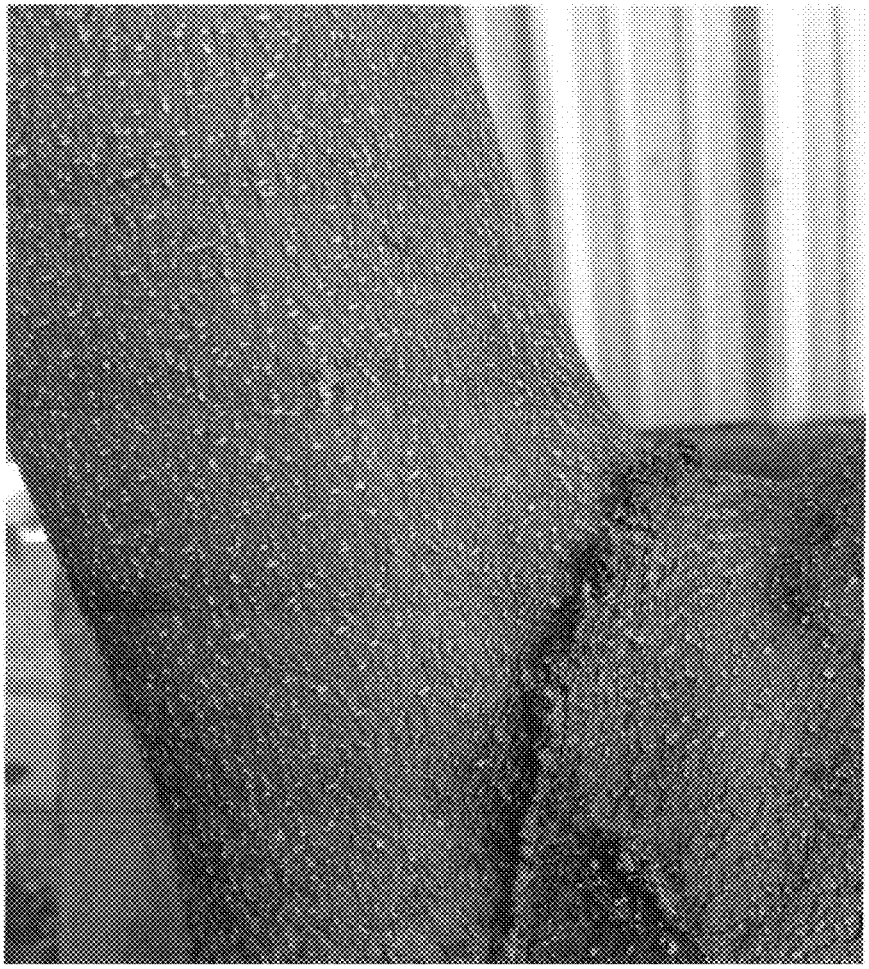
FIG. 3 shows the first branch above the trunk illustrated in FIG. 2.
Figure 4:
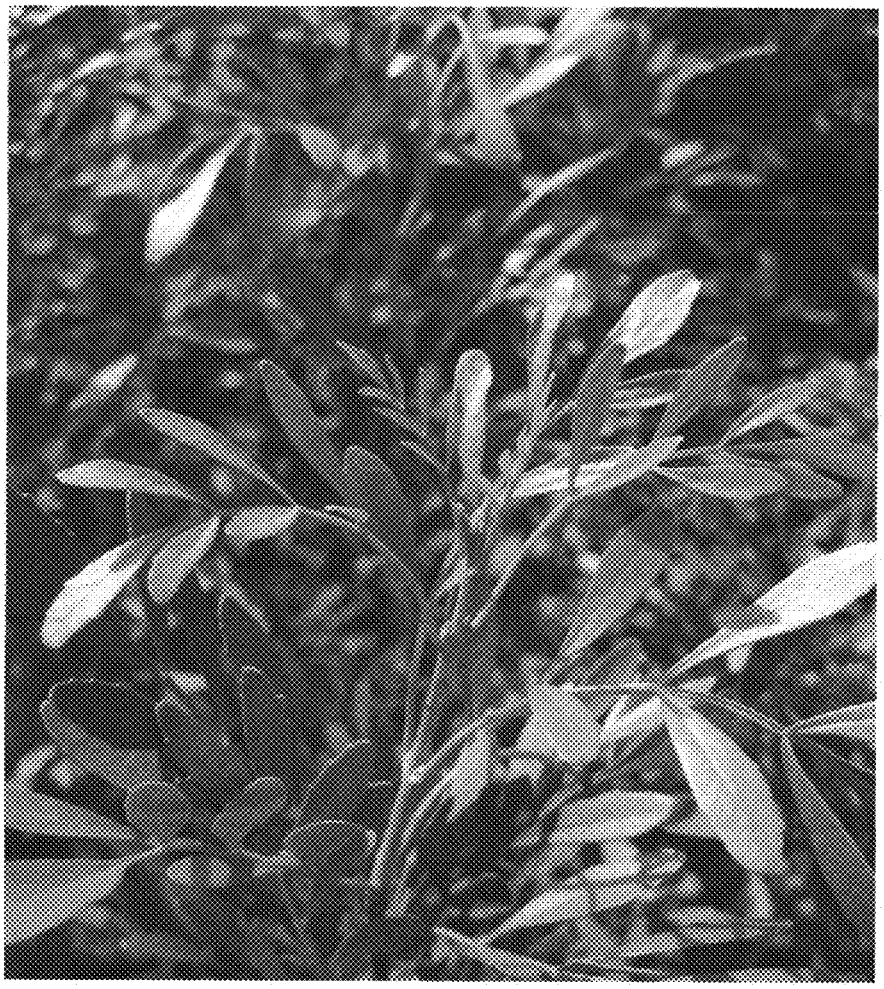
FIG. 4 shows young leaves of *Fraxinus greggii* 'Libby Davidson'.
Figure 5:
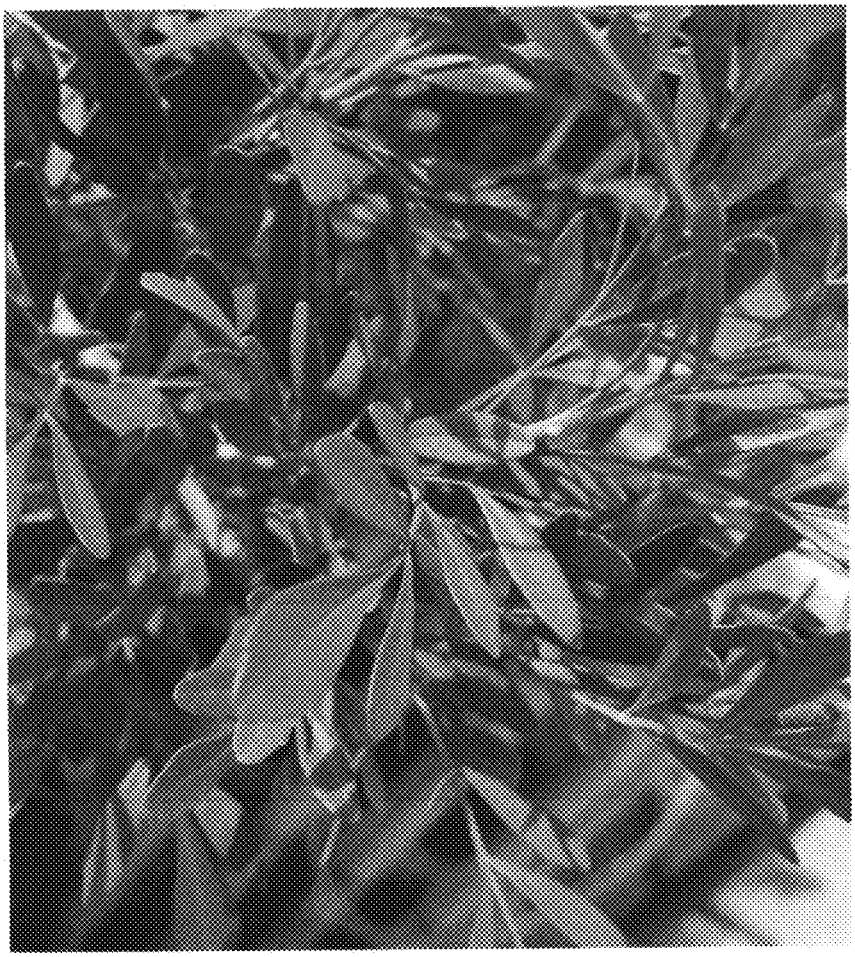
FIG. 5 shows mature leaves of *Fraxinus greggii* 'Libby Davidson'.
Figure 6:
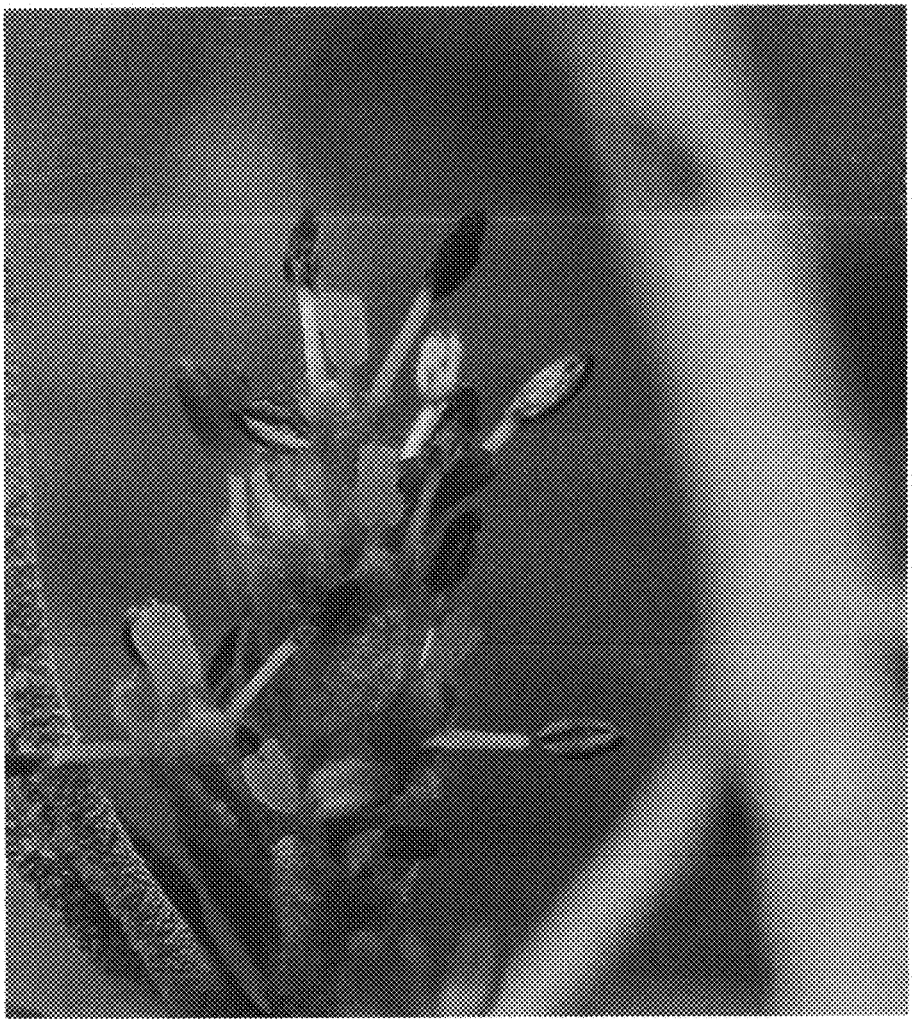
FIG. 6 shows an inflorescence of *Fraxinus greggii* 'Libby Davidson'

The following is a detailed description of the new *Fraxinus greggii* 'Libby Davidson'. The specimen described is a 10 year old plant growing under irrigation near Sahuarita, Ariz. The included color descriptions are based upon the 5$^{th}$ edition R.H.S. Colour Chart. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Form: A multitrunked, small, evergreen tree measuring about 18 ft tall×20 ft wide at age 10.

Trunk: About 6 inches in caliper at the minimum diameter zone between the root swell and first branching (about 8 inches above ground level), bark flakey to somewhat platy, color N187C, with younger bark in cracks and under flakes closest to color 161D.

Branch angle: Between about 40° and 75°.

Stems: Young, but mature stems, cylindrical, 2-3 mm in diameter, color N187C, finely and obscurely puberulous with scattered lenticels; these lenticels colored N170D, more or less elongated longitudinally and rising slightly above the stem surface, from 0.4 mm wide×0.4 mm long to 0.4 mm wide×1 mm long. Internodes vary from 4 to 16 mm in length. Dormant buds 1 mm wide×1 mm long, ovoid, laterally compressed, very finely puberulent, color 164D. Bud scales not discernable. By the time the stem diameter reaches about 1 inch, the bark surface becomes finely elongated reticulate color N187C, the reticulum slightly raised above the general surface. The lenticels (color N187D) at this stage tend to cluster in small groups parallel to the stem axis, varying from 0.4 mm×0.4 mm to 2 mm×1.6 mm, mostly oriented perpendicular to the axis. Older mature bark eventually becoming flakey and somewhat platy, color N187C. Newly forming bark in cracks and under flakes closest to color 161D.

Leaves: Evergreen, opposite leaf arrangement, leaves odd pinnately compound, overall shape roughly ovate; young leaves mealy with sparse puberulent hairs, all deciduous by maturity, ultimately glabrous, somewhat coriaceous and lustrous; leaflets 1-7, mostly 5, the terminal leaflet larger than the laterals; leaflets oblanceolate, obscurely and irregularly toothed; apex of leaflets elliptical, rounded, acute; leaflet bases acuminate. Color of new leaves 143A adaxially, 143C abaxially. Mature leaves color N137A adaxially and 138B abaxially.

Leaf measurements and further details: Leaves 40-79 mm long×18-35 mm wide. Petioles 13-23 mm long, 1 mm wide×1 mm thick, flattened adaxially, rounded abaxially; slightly winged; adaxial surface basally 143B grading to 143C terminally; abaxial surface of petiole colored as the leaves (138B). Leaf rachis, color 139C, first segment 14-16 mm long, 1 mm wide, 0.75 mm thick with a depressed central longitudinal vein, which is colored 139D. Abaxial color same as leaves, color 138B. Terminal leaflets measure from 31-42 mm long×6-9 mm wide. Lateral leaflets measure from 18-26 mm long×5-6 mm wide.

Reproductive structures: Inflorescences axillary, opposite, and paniculate with 1-7 branches each, comprised of 5-30 flowers per inflorescence, flowers hermaphroditic. Inflorescences are 7-15 mm wide by 7-25 mm long, spreading and somewhat cascading. Peduncles measure 1 mm thick×1 mm long, terete, with a mealy surface. The base color is 143A, the flakes of the mealy portion 161A. Inflorescence bracts are paired (opposite) oblong/lanceolate in shape, finely sericeous abaxially, color 161A and 1.5-3 mm long×1 mm wide. Interior of bracts are glabrous, color 151A. Floral bracts appear similar to inflorescence bracts, but of smaller size with somewhat reduced pubescence, measuring 1-1.5 mm long×0.5-0.75 mm wide. Flowers are comprised of 4 sepals fused at the base, without petals, 2 exserted, basifixed stamens and one pistil with 2 stigma lobes. Pedicels measure 2-3 mm long×0.5 mm thick, terete, color 144A with scattered wooly hairs. The cup shaped calyx (measuring 1 mm long×1 mm thick) is comprised of 4 sepals; fused at the base, ovate in shape, 1 mm wide×1 mm long, color 145A. Sepal exterior is covered with scattered wooly hairs, tufted at the apex of the sepal and appearing ciliate in casual view. Sepal interior is glabrous. The corolla is absent. Flowers have two opposing exserted stamens attached to the receptacle, each as follows: Anthers are 2 mm long×1 mm thick, ovate in shape; color varying from 59A to 59C and sometimes grading to 145B to 145C basally. Filament at anthesis measures 1.3 mm long×0.3 mm wide, more or less terete, color 157A. Anthers dehisce longitudinally on 2 lines. Post dehiscence the anther color dries to 187A. Pollen is produced, color 158A. The ovary is superior, with one ovule, 0.3 mm long×0.3 mm thick at anthesis, glabrous, color 145A. The ovary becomes somewhat flattened, 3 ribbed and ovate in shape following pollination. The style measures 0.5 mm long×0.5 mm thick at anthesis, terete, glabrous, color 145A. The stigma is two lobed, the lobes parallel to slightly spreading, roughly oblong in shape, 0.66 mm long×0.33 mm thick at anthesis, terete, color 151A. The stigma darkens to 187B following pollination. No fruits or seeds have been produced in 10 years of growth at the Sahuarita, Ariz. location. The reasons for this are unknown, as the plant seems to produce healthy flowers and pollen. It is speculated that the species may be self-incompatible and since no other blooming plants are growing nearby, no fruit is set.

Diseases and pests: None observed.

COMPARISONS TO RELATED *FRAXINUS*

No selected varieties of *Fraxinus greggii* are known to the inventor. Compared to seed grown Gregg ash, 'Libby Davidson' has improved cold hardiness, evergreen tendency with a faster growth rate and larger, darker green leaves. As a clonally reproduced plant, *Fraxinus greggii* 'Libby Davidson' avoids the crippled plants normally found among seedling Gregg ash and is uniform in growth and form.

I claim:

1. A new and distinct *Fraxinus greggii* plant substantially as described and illustrated herein.

* * * * *